United States Patent
Burzynski et al.

(10) Patent No.: US 7,087,219 B2
(45) Date of Patent: Aug. 8, 2006

(54) TOOTHPASTE CONTAINING ANTICANCER AGENTS

(75) Inventors: Stanislaw R. Burzynski, 20 W. Rivercrest, Houston, TX (US) 77042; Wojciech Gruszecki, Berlin (DE)

(73) Assignee: Stanislaw R. Burzynski, Houston, TX (US)

( * ) Notice: Subject to any disclaimer, the term of this patent is extended or adjusted under 35 U.S.C. 154(b) by 327 days.

(21) Appl. No.: 10/446,536

(22) Filed: May 28, 2003

(65) Prior Publication Data

US 2004/0241107 A1 Dec. 2, 2004

(51) Int. Cl.
A61K 8/00 (2006.01)
A61K 8/21 (2006.01)
A61K 8/40 (2006.01)
A61K 8/41 (2006.01)

(52) U.S. Cl. .............. 424/49; 424/52; 424/54; 433/215; 433/216; 433/228.1

(58) Field of Classification Search ........... 424/49, 424/52, 54; 433/215, 216, 228.1
See application file for complete search history.

(56) References Cited

U.S. PATENT DOCUMENTS

| | | | | |
|---|---|---|---|---|
| 4,470,970 A | 9/1984 | Burzynski | ............ | 424/177 |
| 4,593,038 A | 6/1986 | Burzynski | ............ | 514/328 |
| 4,690,774 A * | 9/1987 | Vishnupad et al. | ............ | 516/29 |
| 4,915,936 A | 4/1990 | Patterson et al. | ............ | 424/49 |
| 4,918,193 A | 4/1990 | Burzynski | ............ | 546/220 |
| 5,589,160 A | 12/1996 | Rice | ............ | 424/49 |
| 5,626,838 A | 5/1997 | Cavanaugh | ............ | 424/54 |
| 5,700,449 A | 12/1997 | Katayama et al. | ............ | 424/49 |
| 5,827,503 A | 10/1998 | Schwabe | ............ | 424/54 |
| 5,932,193 A | 8/1999 | Lopez et al. | ............ | 424/52 |
| 6,123,925 A | 9/2000 | Barry et al. | ............ | 424/49 |
| 6,149,894 A | 11/2000 | Yamane et al. | ............ | 424/49 |
| 6,159,449 A | 12/2000 | Winston et al. | ............ | 424/52 |
| 6,174,515 B1 | 1/2001 | Suhonen | ............ | 424/49 |
| 6,258,849 B1 | 7/2001 | Burzynski | ............ | 514/563 |
| 6,440,397 B1 | 8/2002 | Thomas et al. | ............ | 424/49 |

FOREIGN PATENT DOCUMENTS

| | | |
|---|---|---|
| DE | 199 32 427 | 7/1999 |
| WO | WO 94/09798 * | 8/1994 |

OTHER PUBLICATIONS

Burzynski, S.R., "Antineoplastons: History of the Research (I)" *Drugs Exptl. Clin. Res., Suppl. 1*, 1986, vol. 12; 1-9.
Epstein, J.B. et al., "A double-blind crossover trial of Oral Balance gel and Biotene® toothpaste versus placebo in patients with xerostomia following radiation therapy" *Oral Oncology* 1999, 35; 132-137.
Fairbrother, K.J., et al., "Anticalculus Agents" *Journal of Clinical Periodontology* 2000, 27; 285-301.
Moran, J., et al., "A study to assess the plaque inhibitory activity of a new triclosan mouthrinse formulation" *Journal of Clinical Periodontology* 2000, 27; 806-809.
Nagy, K, et al., "Inhibition of microflora associated with oral malignancy" *Oral Oncology* 2000, 36; 32-36.
Steinberg, D., et al., "Development of Sustained-Release Devices for Modulation of Dental Plaque Biofilm and Treatment of Oral Infectious Diseases" *Drug Development Research* 2000, 50; 555-565.
Warde, P., et al., "A phase II study of Biotene in the treatment of postradiation xerostomia in patients with head and neck cancer" *Support Care Cancer* 2000, 8; 203-208.

\* cited by examiner

*Primary Examiner*—Frederick Krass
(74) *Attorney, Agent, or Firm*—Howrey LLP

(57) ABSTRACT

A novel dentifrice composition is provided for prevention or treatment of carcinoma of the oral cavity, caries and periodontal diseases of the oral cavity. The dentifrice composition contains a partially water-soluble calcium salt, a medicinal composition useful in the treatment of human neoplastic disease, and a hydrophilic or hydrophobic liquid vehicle. A preferred dentifrice composition is a toothpaste comprising gypsum, 3-N-phenylacetylamino-2,6-dione, gypsum, paraffin oil and a mixture of natural flavoring oils. The components of the dentifrice composition act advantageously to allow the composition to remove plaque, tartar, and oral disease-causing bacteria.

18 Claims, No Drawings

TOOTHPASTE CONTAINING ANTICANCER AGENTS

FIELD OF THE INVENTION

The invention relates to dental and oral prophylactics and, more specifically, to dentifrices such as toothpastes and oral washes which exhibit medicinal, prophylactic, and hygienic effects. In particular, a composition for a dentifrice toothpaste containing calcium sulfate dihydrate, mineral oil and 3-phenylacetylamino-2,6-piperidinedione is disclosed.

BACKGROUND OF THE INVENTION

Diseases of the oral cavity are numerous, and include periodontitis, gingivitis, dental caries, halitosis, aphthous ulcers and plaque formation. In many of these diseases, microorganisms have been implicated as causative agents. For example, periodontal diseases, including periodontitis and gingivitis, are caused by bacteria that form plaques on the surfaces of the teeth at the gingival sulcus or pocket. Bacteria known to provoke periodontitis include *Actinobacillus actinomycetemcomitans, Porphyromonas gingivalis, Prevotella intermedia, Bacteroides forsytus,* and *Treponema denticola*. Current methods of treatment depend upon the severity of the disease. In almost all cases, regimens of treatment involving a medicated dentifrice and/or an oral rinse are utilized. Mild cases, such as simple calculus (tartar) buildup, are generally treated by the mechanical removal of the irritants. Interproximal cleaning is also important in maintaining gingival health. It is well known that mild cases of periodontal diseases in time progress to become more severe, and even pedantic cleaning with common dentifrices can only prolong the progression of these diseases. The large variety of toothpastes on the market is evidence to this immanent imperfection. More severe cases are generally treated surgically by the removal of gingival tissue, polishing of the tooth roots, or in some rare cases, splinting of the teeth. In the case of bacterial infection from one of the above-cited bacteria, treatment with both antibiotics and surgery becomes necessary. Most of these latter approaches are both painful and costly.

Prophylactic measures can be taken to forestall the occurrence, or recurrence of periodontal diseases. Known prophylactic measures include regular removal of calculus and plaque and the use of dental floss. Such measures are typically time consuming, and involve a strict regimen of care in order to be effective. For this reason, known prophylactic measures are rarely completely effective in preventing diseases such as periodontal disease.

Similarly, oral carcinomas are one of the most prevalent cancers worldwide. According to recent statistics, cancers of the oral cavity and oropharynx account for approximately 3% of all cancers diagnosed in the United States each year. The survival rate of oral carcinomas is about 50%, and deaths due to oral and oropharyngeal cancers make it one of the ten most common causes of death. The majority of oral cancers are squamous cell carcinomas and most involve the tongue, oropharynx, and floor of the mouth, with the lips, gingiva, dorsal tongue, and palate being less common sites. Typically, surgery and/or radiation therapy are the current treatments of choice for oral cancers. Additionally, chemotherapeutic agents such as cisplatin, bleomycin, 5-FU, docetaxel, interferon alpha, and methotrexate may reduce tumor size and delay metastasis, but to date their use has not had significant positive effects. As a result, most current chemotherapeutic agents are used as adjuncts to standard surgery and/or radiation therapy, and more often in advanced stages of the disease.

Many and varied applications of dentifrice and mouthwash formulations have been described in the patent and medical literature for the use in oral hygiene and for the treatment of periodontal diseases. These formulations generally include a multitude of active ingredients such as fluoride agents, abrasives, and antibacterial agents. Illustrative of these are U.S. Pat. No. 5,374,418, U.S. Pat. No. 5,597,553, U.S. Pat. No. 6,086,372, U.S. Pat. No. 6,123,925, and U.S. Pat. No. 6,331,291.

U.S. Pat. No. 4,915,936 describes a dental hygiene oral rinse composition for the treatment of gingivitis and related periodontal diseases based on a calcium sulfate hemihydrate (beta-form) compound, water as a liquid carrier, alcohol, and other additives. The described formulation further incorporated a humectant to aid in the adherence of the calcium sulfate hemihydrate to teeth and tissue.

Similarly, several patents have suggested formulations for the topical treatment of carcinomas of the oral cavity. For instance, U.S. Pat. No. 5,626,838 describes the use of the NSAID agent ketorolac (5(benzoyl)-2,3-dihydro-1H-pyrrolizine-1-carboxylic acid) for the treatment of primary squamous cell carcinoma, wherein the NSAID (non-steroidal anti-inflammatory drug) agent is in the form of a mouthwash, mouth spray, dental solution/rinse or toothpaste. However, none of these applications have been directed to a composition that would serve as both a prophylactic and a treatment for diseases of the oral cavity and oral carcinomas. Additionally, most of the current formulations described above utilize a variety of compounds that are potentially detrimental to the long-term health of the patients, especially children.

Thus, there exists a need for a dentifrice composition having both oral hygiene and oral carcinoma prophylactic properties, as well as having the ability to be used as a treatment for such maladies. Furthermore, such a dentifrice composition would utilize mostly natural ingredients in order to minimize any long term side effects. The present dentifrice compositions provide these features, and are composed with original, unparalleled components. They are easily prepared from non-toxic, pharmacologically pure materials, and have exhibited effects in the treatment of a variety of oral diseases and hygiene problems. Additionally, it appears that the use of the present dentifrice composition has prophylactic effects with regard to both diseases and carcinomas of the oral cavity.

SUMMARY OF THE INVENTION

Dentifrice compositions containing 3-phenylacetylamino-2,6-piperidinedione, a partially water soluble calcium salt such as calcium sulfate, and a suitable mineral oil liquid vehicle are disclosed. The composition is preferably a toothpaste comprising a dispersion of 3-N-phenylacetylamino-2,6-piperidinedione blended with gypsum, paraffin oil, and flavor oils. The dentifrice compositions have oral hygiene treatment capabilities, as well as a prophylactic effect with regard to periodontal disease, caries, and oral carcinomas.

The use of other suitable vehicles, partially water soluble calcium salts, and amino acid derivatives related to 3-N-phenylacetylamino-2,6-piperidinedione are also envisioned. The concentration of 3-N-phenylacetylamino-2,6-piperidinedione in the dentifrice compositions of the present invention are preferably in the range of about 0.4% to about 5.0% by weight.

In a further embodiment, the present invention relates to a process of preparing a dentifrice composition comprising 3-N-phenylacetylamino-2,6-piperidinedione, a slightly water soluble calcium salt, and a liquid vehicle. This process provides a dentifrice composition capable of both effectively treating diseases of the oral cavity such as periodontal diseases and caries, and exhibiting a prophylactic effect towards oral carcinomas. The compositions are typically applied manually to the desired areas of the oral cavity, preferably in the morning and in the evening. Preliminary studies with the dentifrice compositions of the present invention demonstrate a significant reduction in diseases of the oral cavity such as calculus buildup, caries, gingivitis, and other periodontal disorders. An unexpected result from these preliminary studies was the removal of tobacco- and/or tea and coffee-related teeth stains using the dentifrice compositions described herein, without the need for incorporating harsh abrasives.

DETAILED DESCRIPTION OF THE PREFERRED EMBODIMENTS

The present invention provides dentifrice compositions for alleviating or preventing diseases and/or carcinomas of the oral cavity. The invention is described hereafter in terms of preferred embodiments known at the time of the application. These embodiments represent the best mode contemplated for formulating and preparing the dentifrice compositions of the present invention.

As used herein, term "dentifrice" or "dentifrices" is intended to refer to products which remain in the mouth for a relatively short period of time, in which they are intimately contacted with substantially all surfaces of the teeth, and are then removed. Non-limiting examples of such products include toothpastes, prophylactic pastes, tooth polishes, gels, professional gels and other related products applied by dentists, as well as mouth washes, mouth rinses, dental flosses, chewing gums, lozenges, tablets, edible food products, and the like.

In one preferred embodiment, the compositions of the dentifrice of the present invention are toothpastes, mouth rinse, mouth sprays, and dental solutions. Preferably, the composition is toothpaste or a mouth rinse, and more preferably the dentifrice composition is toothpaste.

It has now been found that calcium salts having at least partial water solubility, in particular calcium sulfate dihydrate, are useful in dentifrice formulations and compositions as soft abrasives and in the removal of plaque and calculus. While not intending to be held by any particular theory, it appears that the calcium ions present when such salts are used in a dentifrice composition can radically decrease, and even stop, plaque and calculus (tartar) buildup. It also appears that calcium ions can stop the demineralization effect of caries and eliminate oral disease causing bacteria without detrimentally effecting the normal microflora in the mouth.

Similarly, while 3-N-phenylacetylamino-2,6-piperidinedione is a useful drug in the treatment of neoplastic diseases, its incorporation into a dentifrice composition is unknown prior to this. According to numerous publications and patents related to this family of compounds (See, for example, Burzynski, S. R., et al., *Drugs Exptl. Clin. Res.* 12 Suppl., 1, 25–35 (1986);), 3-N-phenylacetylamino-2,6-piperidinedione has been shown to be effective in treating a variety of cancers in clinical trials. It beneficially is a completely non-toxic compound, and has even appeared on the market as a food supplement. The addition of 3-N-phenylacetylamino-2,6-piperidinedione to the dentifrice composition of the present invention may provide the composition with prophylactic characteristics with regard to oral carcinomas. Nonetheless, the incorporation of 3-N-phenylacetylamino-2,6-piperidinedione to a dentifrice composition gave the compositions the needed physical properties, e.g. smoothness, needed.

A key active ingredient in the dentifrice formulation of the present invention is a calcium salt having at least partial water solubility, such as calcium sulfate dihydrate (gypsum, $CaSO_4.2H_2O$), pharmaceutical grade. By "at least partial water solubility", it is meant that the calcium salt should have a solubility of at least 0.10 g/100 mL water at 25° C., or a solubility product constant ($k_{sp}$) of at least about $3.1 \times 10^{-7}$ to about $5.0 \times 10^{-5}$ at 25° C. In the event that calcium sulfate is used, the calcium sulfate may be from any natural source, such as gypsum rock, preferably calcined and meeting both FDA and Codex requirements as to purity. Calcium sulfate synthesized from various chemical processes known to those of skill in the art may also be used, such as the by-product chemical gypsum from citric acid manufacture. Additional, non-limiting examples of calcium salts of at least partial water solubility suitable for use in this invention include calcium sulfate, anhydrous calcium sulfate, calcium sulfate hemihydrate ($CaSO_4.\frac{1}{2}H_2O$), calcium malate, calcium tartrate, calcium lactate, calcium mesoxalate, calcium malonate, calcium succinate, calcium glycerophosphate, and mixtures of the foregoing. Preferably, calcium sulfate dihydrate is used as the calcium salt component.

The calcium salt having at least partial water solubility is desirably incorporated into the dentifrice composition of the present invention, such as toothpastes, tooth gels, mouth rinses, and the like in an amount ranging from about 10% to about 80% by weight of the dentifrice composition. Preferably, about 35% to about 70% by weight of the dentifrice composition is a calcium salt having at least partial water solubility.

The preferred medicinal agent for use with the dentifrice of the present invention for the prevention and treatment of periodontitis, caries, oral disease, and carcinomas of the oral cavity or oropharynx is the amino acid analogue 3-N-phenylacetylamino-2,6-piperidinedione (3-[N-phenylacetylaminopiperndine]-2,6-dion]), also known as antineoplaston A10, and its pharmaceutically acceptable salts. However, other related piperidine dione derivatives which are related to 3-N-phenylacetylamino-2,6-piperidinedione are also envisioned to be useful, such as those described in U.S. Pat. No. 5,238,947, which is incorporated herein in its entirety, as well as the pharmaceutically acceptable salts thereof.

3-N-Phenylacetylamino-2,6-piperidinedione can be isolated from human body fluids, such as urine, as described in U.S. Pat. No. 4,558,057. Alternatively, it can be synthesized by reacting the amino acid L-glutamine with a phenylacetyl halide in a weakly alkaline aqueous solution, lowering the pH of the solution, and subsequently heating the mixture under vacuum at 160° C. to yield 3-N-phenylacetylamino-2,6-piperidinedione, as described in U.S. Pat. No. 4,918,193 and U.S. Pat. No. 4,470,970, both of which are herein incorporated by reference.

As described herein, "pharmaceutically acceptable salts" means salts having the biological activity of the parent compound and lacking toxic activity at the selected administration level. Again, determination of whether a salt is pharmaceutically acceptable can be accomplished by methods known to those of skill in the art. Pharmaceutically acceptable salts of 3-N-phenylacetylamino-2,6-piperidinedione include, but are not limited to, inorganic sodium, potassium and ammonium salts, and organic diethanolamine, cyclohexylamine, and amino acid salts. Preferably, the salt is a sodium salt.

Suitable acids for forming acid addition salts of the compounds of the present invention include, but are not limited to, acetic, tartaric, hydrochloric, citric, fumaric, gluconic, glucuronic, glutamic, lactic, malic, maleic, pamoic, salicylic, stearic, succinic, and tartaric acids. The class of acids suitable for the formation of nontoxic, pharmaceutically-acceptable salts is well known to practitioners of the pharmaceutical formulation arts. (See, e.g, Stephen N. Berge, et al., *Journal of Pharmaceutical Sciences*, Vol. 66; pp. 1–19 (1977); and, P. Heinrich Stahl, et al., *Handbook of Pharmaceutical Salts: Properties, Selection, and Use*, Wiley-VCH, 2002).

Further, the compounds of the present invention can exist in unsolvated as well as solvated forms with pharmaceutically-acceptable solvents such as water, ethanol, and the like. In general, the solvated forms are considered equivalent to the unsolvated forms for the purposes of the present invention.

In the present invention, the amount of antineoplaston A10 (3-N-phenylacetylamino-2,6-piperidinedione) present in the dentifrice composition can be in the range of about 0.1% by weight to about 5.0% by weight. Preferably, the 3-N-phenylacetylamino-2,6-piperidinedione is present in the range of about 0.4% by weight to about 4.5% by weight.

A further component of the dentifrice composition of this invention are hydrophilic liquid vehicles, including but not limited to glycerin, propylene glycol, polyethylene glycol, and hydrophobic liquid vehicles such as triglyceride, diglyceride, and organic oils including mineral oil, essential oils, and fatty vegetable oils. Essential oils, as used herein, are natural substances which are extracted via distillation from tiny molecular sacs of each boltanical, and are part of the plant's immune system and yet a separate substance created from the plant. The distillation process extracts the volatile oil from the plant parts. Such essential oils are highly concentrated extracts that contain hormones, vitamins and antiseptics that work on many levels. Preferably, the liquid vehicle is mineral oil. These hydrophilic and hydrophobic liquid vehicles can be used either singly or in combination and preferably, can be added in a proportion of from about 2 to about 50 wt. % (in the case of compositions comprising liquid vehicles), especially from about 10 to about 35 wt. % based on the whole composition.

Using one or more of these liquid vehicles, the composition of the present invention for the oral cavity may preferably be formulated into a use form such as gel, liquid, or paste.

The dentifrice composition of the present invention also contains flavor components, typically in the form of natural flavors or aroma oils and/or herbal extracts and oils. These flavor components can serve not only to give a palatable flavor to the dentifrice composition, but can act as natural antibacterial agents and preservatives at the same time. The oils suitable for use in the present invention include but are not limited to citric oil, lemon oil, lime oil, lemongrass oil, orange oil, sweet orange oil, grapefruit oil, pomegranate oil, apricot oil extract, tangerine extract, tangelo oil, peppermint oil, spearmint oil, sage oil, rosemary oil, cinnamon oil, winter green oil, clove oil, eucalyptus oil, ginger oil, sassafras oil, menthol, arvensis mint oil, synthetic mint flavors and oils, carvone, eugenol, methyleugenol, methyl salicylate, methyl eugenol, thymol, anethole, millefolium extract, chamomile, lavender oil, myrrh, eugenol, tea tree oil, sage oil, mallow, limonene, ocimene, n-decyl alcohol, citronellol, α-terpineol, linalol, ethyllinalol, thyme, almond oil, nutmeg, and vanillin. Either one of these flavors or a mixture of two or more of these flavors can be used in the dentifrice composition. The content thereof ranges from about 3% to about 20% by weight, preferably from about 4% to about 15% by weight, based on the whole composition.

Silica abrasives can also be incorporated into the dentifrice composition of the present invention, without detracting from the scope of the invention. Specific silica abrasives suitable for use with the present invention include but are not limited to silica gels, precipitated silicas, silicates, and hydrated silica. Silica gels suitable for use with the present invention are hydrogels, hydrous gels, xerogels, and aerogels, such as those known in the art and described in U.S. Pat. No. 6,440,397, which is incorporated herein by reference. Precipitated silicas are those known in the art, such as the suitable dentifrice-type precipitated silicas described in U.S. Pat. No. 5,589,160, the contents of which are incorporated by reference. Suitable silicates are any of those naturally occurring or synthetic silicates suitable for use with dentifrice compositions. These silica abrasives can be used singly or in combination. The preferred silica abrasive for use with the present invention includes silica gels. The silica abrasives can be used together with the calcium salt or in lieu of the calcium salt component.

Water can optionally be incorporated into the present toothpaste compositions of the present invention. Water used in the preparation of commercially suitable toothpastes should preferably be deionized and free of organic impurities. Water can generally comprise about 0% to about 40% by weight of the toothpaste compositions herein.

In addition to the above-described essential components, the dentifrice composition of the present invention can further contain a variety of optional ingredients and vehicles generally used for preparations for use in the oral cavity, such as dentifrices. These optional components include, but are not limited to, such components as abrasives, surfactants, thickening agents, buffers, humectants, preservatives, and antibiotic and anti-caries agents. All of these additives, described in further detail below, are generally usual and would be known to one of skill in the art.

Dental abrasives useful in the dentifrice compositions of the present invention include a variety of different materials known in the art. Preferably, the abrasive material should be one which is compatible with the composition of interest and does not excessively abrade dentin. Suitable abrasives include for example, silicas including gels and precipitates; insoluble polymetaphosphate, hydrated alumina, resinous abrasives such as polymerized resins (e.g. ureas, melamines, cross-linked epoxies, phenolics, and the like), and mixtures thereof.

Another optional component of the dentifrice compositions of the present invention is a humectant. The humectant serves to keep compositions such as toothpaste compositions from hardening upon exposure to air, and to give mouthwash and toothpaste compositions a moist feel to the mouth. Certain humectants can also impart desirable sweetness of flavor to toothpaste and mouthwash compositions. Suitable humectants for use in compositions of the present invention include edible polyhydric alcohols such as glycerin, sorbitol, xylitol, polyethylene glycol, and propylene glycol.

The dentifrice compositions of the present invention can also optionally contain sweeteners such as saccharin sodium, acesulfame potassium, glycyrrhizin, perillartine, thaumatin, aspartylphenylalanyl methyl ester and xylitol.

Buffering agents are another optional component of the dentifrice compositions of the present invention. The buffering agents serve to retain the pH of the compositions within the preferred range. Suitable buffering agents for use in dentifrice compositions of the present invention include soluble phosphate salts.

Other optional components of the dentifrice compositions of the present invention are preservatives, such as those that prevent microbial growth in the dentifrice compositions. Suitable preservatives include but are not limited to methylparaben, propylparaben, bezoates, and alcohols such as ethanol.

Binders and thickeners can also optionally be used in the dentifrice compositions of the present invention, particularly in toothpaste compositions. Preferred binders and thickening agents include, but are not limited to, carrageenan (e.g. Viscarin, Irish moss, and the like); cellulose derivatives such as hydroxyethyl cellulose, sodium carboxymethyl cellulose, and sodium carboxymethyl hydroxypropyl cellulose, carboxyvinyl polymers; natural gums such as karaya gum, gum Arabic, and tragacanth; polysaccharide gums such as xanthan gum; fumed silica; and colloidal magnesium aluminum silicate.

Compositions of the present dentifrice compositions can also optionally contain a surfactant. Suitable surfactants are those which are reasonably stable and preferably form suds (bubbles) throughout the pH range of the dentifrice compositions. Surfactants can also be added to act as solubilizing agents to help retain sparingly soluble components in solutions or mixtures. Surfactants useful in the dentifrice compositions as sudsing agents can be soaps, polysorbates, poloxamers, and synthetic detergents that are anionic, nonionic, cationic, zwitterionic, or amphoteric, and mixtures thereof.

The dentifrice compositions of the present invention can also optionally comprise anti-caries agents. Preferred anticaries agents are water-soluble fluoride ion sources. The number of such fluoride ions sources is great and well known to those of skill in the art, and includes those disclosed in U.S. Pat. No. 3,535,421, which is incorporated herein by reference. Preferred fluoride ion source materials include sodium fluoride, potassium fluoride, sodium monofluorophosphate and mixtures thereof.

Antimicrobial and anti-plaque agents can also optionally be present in the dentifrice compositions of the present condition. Such agents may include: triclosan (5-chloro-2-(2,4-dichlorophenoxy)-phenol); chlorhexidine; chlorhexidine digluconate (CHX); alexidine, hexetidine (HEX); sanguinarine (SNG); benzalkonium chloride; salicylanilide; domiphen bromide; cetylpyridiniumchloride (CPC); tetradecylpyridinium chloride (TPC); N-tetra-decyl-4-ethylpyridinium chloride (TDEPC); octenidine; delmopinol; octapinol, and other piperidino derivatives; nicin preparations; zinc/stannous ion agents; antibiotics such as augmentin, amoxicillin, tetracycline, deoxycycline, minocycline, and metronidazole; peroxide, such as cylium peroxide, hydrogen peroxide, and magnesium monoperthalate an its analogs; and analogs and salts of the above listed antimicrobial and antiplaque agents.

Dentifrice compositions of the present invention can also optionally include one or more anticalculus (anti-tartar) agents. Anticalculus agents which may be useful in the dentifrice compositions of the present invention include antimicrobials such as chlorhexidine, niddamycin, and triclosan, metals and metal salts such as zinc citrate, Vitamin C, bisphosphonates, triclosanpyrophosphates, pyrophosphates, polyphosphates, polyacrylates and other polycarboxylates, polyepoxysuccinates, ethyenediaminetetraacetic acid (EDTA), nitrilotriacetic acid and related compounds, polyphosphonates, and polypyrophosphates such as sodium hexametaphosphate, as well as other anticalculus agents known to those of skill in the art, such as those described in K. J. Fairbrother et al., "Anticalculus agents," *Journal of Clinical Periodontology* Vol. 27, pp. 285–301 (2000).

Nutrients and vitamins can also optionally be added to the dentifrice compositions of the present invention. Such agents can include folates, retinoids (Vitamin A), Vitamin B ($B_1$-thyamin, $B_2$-riboflavin, $B_3$-niacine, $B_5$-pantothenic acid, $B_6$-pyridoxine, $B_7$-biotin, $B_8$/$B_9$/Bc-folic acid, $B_{12}$-cyanocobalamin), Vitamin C (ascorbic acid, sodium ascorbate), Vitamin E, Vitamin E analogs (dl-α-tocopherol acetate, tocopherol succinate, tocopherol nicotinate)and zinc.

A variety of miscellaneous additives can also be optionally formulated into the dentifrices of the present invention, such as tooth desensitizing agents (e.g. potassium and strontium salts), condensed anti-tartar agents such as sodium and potassium tetrapyrophosphate, whitening agents such as aluminum oxide and calcium peroxide, debriding agents such as sodium bicarbonate, pigments and dyes, such as Blue 15-C174160, Green 7-C174260, Reds 4-CI12085 and 40 CI16035, Yellows 115 CI47005:1 and 5 CI19140, and Carmine 5 CI16035), as well as additives such as mica and sparkles. As with the other optional dentifrice additives, use can be made of either one of these ingredients or a mixture of two or more of these ingredients in amounts appropriate for the dentifrice composition.

An unexpected cleaning performance of this invention has also been demonstrated. The dentifrice of the present invention has surprisingly exhibited the ability to remove tar deposits related to tobacco use from the teeth and other surfaces of the oral cavity, as well as stains on the teeth due to coffee and/or tea consumption. It is well known that the use of tobacco products deposits a constituent commonly referred to as "tar" within the oral cavity. Tobacco tar, as used herein, is loosely defined as a dark, oily, viscous blend of polycyclic aromatic and aliphatic hydrocarbons, as well as other compounds. Tar is produced as tobacco in a cigarette, cigar, or pipe is burned, and as tobacco is chewed. This tar readily forms a solution with saliva, and enzymes in the saliva assist in the degradation of tobacco itself. The tobacco and saliva-tar solution, as well as materials contained therein, can be deposited on the surfaces within the oral cavity of the tobacco users, leaving resinous stains.

Due to the hydrophobic nature of compounds contained within the tar, the tar is not easily dissolved, solubilized, detached, and/or dispersed by commonly available, over the counter dentifrices such as toothpastes, gels, and oral rinses. As a result, tobacco tar can buildup on the teeth and other surfaces of tobacco users' oral cavities, causing chronic halitosis, increased calculus (tartar) buildup, and an increased incidence of periodontal diseases, as wall as unsightly staining.

Prior to the present invention, the known anti-tobacco/tar stain products on the market were dentifrices such as toothpastes which did not contain ingredients with the ability to dissolve, solubilized, or otherwise remove tobacco stains or tar, but rather, removed tobacco stains and tar deposits through the presence of physical abrading agents. Unfortunately, such abrading materials, which are strong enough to remove tobacco stains and tar buildup, also tend to abrade tooth enamel and can promote tooth decay and further oral diseases.

It has been unexpectedly found that the dentifrice composition of the present invention has the ability to reduce tar buildup and stains due to tobacco use, as well as stains due to coffee and/or tea consumption, without the use of a strong abrasive component. As indicated above, the combination of a slightly water soluble calcium compound with a liquid vehicle and the antineoplaston A10 (3-N-phenylacetylamino-2,6-piperidinedione) provides a composition that easily emulsifies with saliva in the mouth and readily cleans the surfaces of the oral cavity without the use of harsh abrasives. Patients who were tobacco users, coffee and/or tea consumers, or both, and who used a toothpaste having the composition of the present invention exhibited noticeable stain removal.

The composition according to the present invention may preferably be used by applying it into the oral cavity and brushing the teeth and/or gingivae. For such brushing, use of a toothbrush provided with plaque removing bristles and gingiva-massaging portions in combination is especially preferred, although a conventional toothbrush, namely, a toothbrush having plaque removing bristles or a toothbrush having massaging portions may also be used.

In the process for preparing the dentifrice toothpaste of the present invention, the first step is the preparation of the oil component. In the preparation of the oil component, one or more natural flavor or aroma oils are added to a volume of a liquid vehicle, such as paraffin oil. The mixture is stirred, either mechanically or by hand, for a time sufficient to form a homogenous mixture. It is generally preferred that the temperature of the mixture be maintained at or near ambient temperature during the preparation.

For the preparation of the toothpaste, the homogenous oil mixture is stirred with a) an appropriate slightly water-soluble calcium salt or a mixture of calcium salts; b) 3-phenylacetylamino-2,6-piperidinedione; and c) optionally, water or other vehicle, (e.g. glycerin), in order to obtain a complete toothpaste formulation. In a preferred method of preparation, the flavor and aroma oils are added together and then brought up to the desired volume with the liquid vehicle. This flavor oil/vehicle solution is then stirred together until the mixture is homogenous. Thereafter, the calcium salt and 3-N-phenylacetylamino-2,6-piperidinedione are ground together to form a homogenous powder. This homogenous powder is then stirred together, mechanically or by hand, with the oil mixture until a smooth paste forms. The paste can then be packed into tubes in a manner known to those of skill in the art.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Toothpaste Formulation Containing Calcium Sulfate Dihydrate and About 0.5 wt. % of 3-phenylacetylamino-2,6-piperidinedione A toothpaste formulation according to the present invention was prepared as follows.

To an appropriate measuring container was added 6 mL of grapefruit oil, 2 mL of citric oil, 2 mL of sweet orange oil, 2 mL of peppermint oil, and 2 mL of eucalyptus oil, and the flavor oils mixed at ambient temperature. Thick liquid paraffin [Food Grade] (also known as mineral oil) was then added in an amount sufficient to bring the total volume of the mixture up to 100 mL. The oil component was mixed so as to form a homogenous solution. This is the base flavoring oil component for use in the toothpaste examples described herein.

To 30 g of finely powdered gypsum (calcium sulfate dihydrate; pure for the food production industry) was added 0.2 g 3-phenylacetylamino-2,6-piperidinedione as a dry, solid powder. The two solids mixed to form a homogenous solid, and then 12 g of the flavoring oil component from above was added. The composition of the powders and oils was mixed together to form a smooth paste. The paste was then packed into a tube.

Example 2

Toothpaste Formulation Containing Calcium Sulfate Dihydrate and About 5.0 wt. % of 3-phenylacetylamino-2,6-piperidinedione The paste composition in Example 1 was reformed, this time using 2.2 g of 3-phenylacetylamino-2,6-piperidinedione, in the same manner as described. The paste was formed into a smooth paste, as before, and packed into a tube. The toothpaste of this formulation had a slightly bitter taste.

Example 3

Toothpaste Formulation Containing Calcium Sulfate Dihydrate, About 5.0 wt. % of 3-phenylacetylamino-2,6-piperidinedione, and Glycerine To 60 g of finely powdered gypsum (as in Example 1) was added 1.2 g of 3-phenylacetylamino-2,6-piperidinedione as a dry powder, and the two solids were mixed together to form a homogenous powder. This solid powder was then mixed with 32 g of the oil component (as prepared in Example 1) for 30 minutes. A smooth, half-liquid paste results. To this paste was added 4 g of glycerin (available from numerous commercial sources), and the mixing continued for a further 30 minutes. The product paste was packed into small (20 g) aluminum tubes, and was ready for use. The toothpaste of this formulation had a pleasant, sweet taste.

Example 4

Clinical Study of the Dentifrice Composition

In a test of examination of the stability of the new paste, 30 test subjects varying in age from 15 to 65, both genders, used the toothpaste prepared according to either Example 1 or Example 2 over a one month period as their sole toothpaste. The individuals cleaned their teeth two times daily, once in the morning and again in the evening following their last meal. The individuals were under dentist supervision throughout, as well as during the initial and final examinations. None of the individuals reported intolerance or hypersensitivity to the new toothpastes. In all of the test subjects, the dental examiner found significant reduction of plaque. All subjects reported clean teeth and improved mouth hygiene all day. Those test subjects who were tobacco users (smokers, chewing tobacco) or heavy tea/coffee drinkers exhibited none of the stains typically found on the teeth that are consistent with tobacco or coffee/tea use.

Example 5

Clinical Treatment of Oral Disease with the New Dentifrice Composition

Four adult individuals with advanced periodontitis, gum bleeding, and plaque buildup were given toothpaste formulated according to Example 1 for use two times daily, after meals. After several days, the gum bleeding had stopped. After two weeks of use, the stony plaque buildup on the tooth surface had diminished. Dental examination confirmed the arrest of the periodontitis progress in all four adults.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

What is claimed is:

1. A toothpaste composition, comprising:
   a calcium salt having at least partial water solubility;
   at least one flavoring oil;
   a liquid vehicle; and
   3-N-phenylacetylamino-2,6-piperidinedione or pharmaceutically acceptable salts thereof.

2. The toothpaste composition of claim 1, wherein the calcium salt is selected from the group consisting of calcium sulfate, anhydrous calcium sulfate, calcium sulfate hemihydrate, calcium sulfate dihydrate, calcium malate, calcium tartrate, calcium malonate, and calcium succinate.

3. The toothpaste composition of claim 1, wherein the calcium salt is calcium sulfate dihydrate.

4. The toothpaste composition of claim 1, wherein the liquid vehicle is a hydrophobic liquid vehicle or a hydrophilic liquid vehicle.

5. The toothpaste composition of claim 1, wherein the liquid vehicle is selected from the group consisting of glycerin, propylene glycol, polyethylene glycol, triglyceride, diglyceride, mineral oil, organic oils, essential oils, fatty vegetable oils, and combinations thereof.

6. The toothpaste composition of claim 1 wherein the liquid vehicle is mineral oil.

7. The toothpaste composition of claim 1 wherein the liquid vehicle is a combination of glycerin and mineral oil.

8. The toothpaste composition of claim 1, wherein the 3-N-phenylacetylamino-2,6-piperidinedione is present in an amount of about 0.1 wt. % to about 5 wt. % of the total composition.

9. The toothpaste composition of claim 1, wherein the calcium salt is present in an amount of about 35 wt. % to about 70 wt. % of the total composition.

10. A toothpaste composition comprising:
a silica abrasive, and
3-N-phenylacetylamino-2,6-piperidinedione or pharmaceutically acceptable salts thereof.

11. The toothpaste composition of claim 10, wherein the silica abrasive is selected from the group consisting of silica gels, precipitated silicas, silicates, and hydrated silica.

12. The toothpaste composition of claim 11, wherein the silica gel is selected from the group consisting of hydrogels, xerogels, and aerogels.

13. The toothpaste composition of claim 10, wherein the 3-N-phenylacetylamino-2,6-piperidinedione is present in an amount of about 0.1 wt. % to about 5 wt. % of the total composition.

14. The toothpaste composition of claim 10, wherein the composition contains at least one flavoring oil.

15. A method for removing tobacco tar and/or tea and coffee deposits on surfaces in the oral cavity resulting from the introduction into the oral cavity of tobacco tar, tea, and/or coffee, the method comprising the steps of:
introducing into the oral cavity a toothpaste composition comprising a partially water soluble calcium salt, a liquid carrier, 3-N-phenylacetylamino-2,6-piperidinedione or pharmaceutically acceptable salts thereof; and brushing surfaces in the oral cavity with a toothbrush thus removing said deposits.

16. The method of claim 15, wherein the concentration of the partially water soluble calcium salt is about 35% to about 70% by weight of the total composition.

17. The method of claim 15, wherein the partially water soluble calcium salt is calcium sulfate dihydrate.

18. The method of claim 15, wherein the concentration of 3-N-phenylacetylamino-2,6-piperidinedione is about 0.1% to about 5.0% by weight of the total composition.

* * * * *